United States Patent [19]

Smart, Jr. et al.

[11] Patent Number: 5,165,930

[45] Date of Patent: Nov. 24, 1992

[54] BIOLOGICAL CONTROL OF MOLE CRICKETS (SCAPTERISCUS SPP.)

[75] Inventors: Grover C. Smart, Jr.; Nguyen B. Khuong, both of Gainesville, Fla.; H. G. Fowler, Sao Paulo, Brazil

[73] Assignee: University of Florida, Gainesville, Fla.

[21] Appl. No.: 453,806

[22] Filed: Dec. 20, 1989

Related U.S. Application Data

[63] Continuation-in-part of Ser. No. 406,825, Sep. 12, 1989, abandoned, which is a continuation of Ser. No. 895,385, Aug. 11, 1986, abandoned.

[51] Int. Cl.$^5$ .................. A01N 63/00; A01N 25/00; A61K 35/56
[52] U.S. Cl. .................. 424/93 R; 424/405; 800/2; 119/6.7
[58] Field of Search .............. 424/93, 405, 93 R; 119/6.7; 800/2

[56] References Cited

PUBLICATIONS

Smart et al. 1984 in: *First International Congress of Nematology*, Guelph, Ont., Canada, Aug. 5–10, 1984, p. 95, abstract 253.
*International Rice Newsletter*, vol. 13, 34–35.
Shapiro et al. 1985, J. Elon. Entomol. 78, 342–345.

Primary Examiner—Robert A. Wax
Assistant Examiner—Christopher S. F. Low
Attorney, Agent, or Firm—Kerkam, Stowell, Kondracki & Clarke

[57] ABSTRACT

Method, composition and product for controlling pest insects in the Order Orthoptera based on the insecticidal nematode *Steinernema scapterisci*.

3 Claims, No Drawings

BIOLOGICAL CONTROL OF MOLE CRICKETS (SCAPTERISCUS SPP.)

RELATED APPLICATIONS

This is a continuation in part of application Ser. No. 406,825 filed Sep. 12, 1989, now abandoned, which was a continuation of Ser. No. 895,385, filed Aug. 11, 1986, now abandoned.

BACKGROUND OF THE INVENTION

1. Field of the Invention

The present invention relates to the biological control of mole crickets (Scapteriscus spp.).

2. Prior Art

The mole crickets, *Scapteriscus acletus, S. vinicus* and *S. abbreviatus* were introduced accidentally into Florida from South America, (Walker and Nickle, 1981, Ann. Entomol. Soc. Am. 74:158-163). It has been reported that there is no economical method of controlling mole crickets in the United States (Nickle and Castner, 1984, Ann. Entomol. Soc. Am. 77:450-465)]. Chemical control with insecticides has been attempted [Ismailov et al., Zashch. Rast. (Moscow) 160:32 (1981); Loutfy et al., Agric. Res. Rev. 55(1):193-5 (1977); Noguchi et al., Shikoku Shokubutsu Boeki Kenkyci, 11:23-8 (1976); Bastos et al., Fitossamidade, 2(2):57-8 (1977); Short, Down Earth, 29(1):26-29 (1973); Chari et al., Pesticides, 7(3):16-17 (1973); Vinnichenko, Tr. Kishinet, Selskehoz. Inst. 88:90-2 (1972); Vinnichenko, ibid, 66:182-91 (1971); Van Middelem et al., J. Econ. Entomol., 65(2):495-7 (1972); Beck et al., ibid, 60(6):1517-19 (1967)] but has not proved practical because of the cost of treating an area, and the need for retreatment due to reinvasion of mole crickets from untreated areas into the treated areas.

It is known that the infective stages of certain nematodes are insecticidal to certain insects. It has been suggested to utilize various insect-parasitic nematodes for biologically controlling various insects. U.S. Pat. No. 4,178,366 discloses an insecticidal composition containing infective larvae of the nematode *Neoaplectana carpocapsae* (Agriotos strain for biologically controlling a wide variety of insects such as the codling moth (*Cydia pomonella*), the southern ironbark beetle (*Dendroctonus frontalis*), larch sawfly larvae (*Pristophora erichsonii*), Colorado potato beetle (*Leptinotarsa decemlineata*), cabbage white butterfly (*Pieris rapae*), cutworms (*Persectania ewingi* and Euromessoria sp.), eucalyptus sawflies (*Perga affinis* and Pterygophorus), the cup moth (Doratifera sp.), the autumn gum moth (*Mnesampela privata*) and the chrysomelids, *Chrysophtharta nobilitata, C. decolorata, C. aureous, Paropsisterna nucea, Paropsis lutea* and *P. charybdis*.

U.S. Pat. No. 4,615,883 describes an insecticidal composition containing nematodes having insecticidal activity against a wide variety of insects.

Serczynska [Bull. Acad. Pol. Sci. Ser. Sci. Biol., 26(2):103-6 (1978)] reports that a composition of tribunil and *Neoaplectana carpocapsae* (Weiser) was effective against the Colorado beetle.

Burman [Nematologica, 28(1):62-70 (1982kl)] reports on the insecticidal toxin produced by the nematode *Neoaplectana carpocapsae*.

Fowler et al. [Rev. Brasil. Biol., Vol. 43, pp. 789-795 (Nov. 1988); Naturwirrenschaften, Vol. 76, pp. 26-27 (1989) and Intl. Rice Research Newsletter, Vol. 13, pp. 34-35 (1988)] report on research directed toward the control of, among others, mole crickets utilizing the nematodes *Steinerema feltiae.*

Biosys, Inc., currently markets a product called "BioSafe," containing *Neoaplectana carpocapsae* (=*Steinerema feltiae*, strain All) which is said to be useful for controlling mole crickets. A disadvantage associated with this strain, however, is that it does not reproduce in mole crickets and cannot, therefore, recycle in nature.

The utilization of insect-parasitic nematodes for biologically controlling insects suffers from several other disadvantages however.

Thus, most strains of the nematode, *Neoaplectana carpocapsae* demonstrate little host specificity and will parasitize, infect with toxin and kill a wide variety of insects. Where it is desired to kill only a certain or a few species of insects, most strains of nematodes generally represent a poor choice for biological control since they may infect and kill beneficial insects as well.

It is an object of the present invention to provide an insecticidal composition and a method of controlling pest insects in the Order Orthoptera, e.g., cockroaches, grasshoppers, locusts, and, in particular, mole crickets, utilizing a heretofore unknown nematode.

SUMMARY OF THE INVENTION

The foregoing and other objects are realized by the present invention which provides a method of biologically controlling pest insects in the Order Orthoptera comprising contacting so as to infect the insects with an insecticidal amount of infective third stage of *Steinernema scapterisci* nematodes.

A further embodiment of the invention comprises a composition for the biological control of pest insects in the Order Orthoptera comprising an insecticidally effective amount of infective third stage of *Steinernema scapterisci* nematodes and an inert carrier therefore.

DETAILED DESCRIPTION OF THE INVENTION

The research, which led to the description of the invention in parent application Ser. No. 895,385 erroneously characterized the mole cricket infective nematode as *Steinernema carpocapsae* (=*Neoaplectana carpocapsae*=*Steinernema feltiae*). Further research of the biology and morphology of the nematode has revealed that the nematode is not *S. carpocapsae*, but rather a heretofore unknown species, designated *Steinernema scapterisci.* The nematode, a natural enemy of the mole cricket, was found in Brazil and Uruguay.

The genus *Steinernema* was erected by Travassos in 1927 (Travassos, L. 1927, Sobre o Genera Oxysomatium, Boletim Biologico 5:20-21) to contain the species *Aplectana kraussei* which Steiner (Steiner, G. 1923, n. sp., eine in der Blattwespe Lyda sp. Parasitierende Nematodenform, nebst Bemerkugen uber das Seitenorgan der parasitichen Nematoden. Centralblatt fur Bakterien und Parasitenkunde 59:14-18) had described in 1923 from the sawfly, *Cephaleia abietis.* Travassos created the new genus because of differences in morphology and because this species was a parasite of insects while all other species in the genus Aplectana were intestinal parasites of Amphibiae.

Steiner [Journal of the Washington Academy of Science, 19:436-440 (1929)] established the genus Neoplectana in 1929 to contain the type species *N. glaseri* which he described from the Japanese beetle (*Popillia*

*japonica*. Later, other species, such as *N. feltiae* Filipjev, 1934 from the cutworm, *N. bibionis*, Bovien, 1937 from bibionid larvae, and *N. carpocapsae*, Weiser, 1955, from the codling moth were added to the genus. Poinar [Poinar, G. O. Jr., 1979, Nematodes for biological control of insects, Boca Raton, Fl.: CRC Press], revised the genus Neoaplectana adding more details to the description of some species and constructing a key to identify the species contained in the genus. According to Filipjev [1934, Miscellanea Nematologica, I. Eine neue Art der Gattung Neoaplectana nebst Bemerkungen uber die systematische Stellung der letzteren. Magazin fur Parasitologie des Zoologischen Instituts der Akademie der Wissenschaften der UdSSR 4:229-240] and other authors [Bedding, R. A., 1984, Nematode parasites of Hymenoptera, pp. 755-795 in W. R. Nickle, ed. Plant and insect parasitic nematodes. New York: Marcel Dekker; Mrazek, Z., J. Weiser and S. Gerdin, 1981. Head and cuticular structures of some species in the family Steinernematidae (Nematoda). Nematologica 27:443-448; Wouts, W. M., 1984, Parasites of lepidopterans, pp. 655-696 in W. R. Nickle, ed. Plant and insect parasitic nematodes, New York: Marcel Dekker], Neoaplectana closely resembles Steinernema. Wouts et al. [1982; Neaplectana Steiner, 1929 a junior synonym of Steinernema Travassos, 1927 (Nematoda: Rhabditida), Systematic Parasitology 4:147-154] demonstrated to their satisfaction that the two genera are identical and thus considered Neoaplectana a junior synonym of Steinernema. We concur with these authors and use the generic name Steinernema for the new species described herein as well as for other species of this group.

Third stage infective nematodes of the genus Steinernema carry with them in the anterior part of the intestine a pellet of live bacteria. *S. scaperisci* carries a bacterium which is probably a new species in the genus Xenorhabdus. When the third stage (the third stage is the only infective stage, i.e., capable of entering an insect) enters the host, usually through its mouth, the nematode goes to the intestine of the insect, penetrates through the intestinal wall and enters the body cavity which is filled with the body fluid (haemolymph). In the body cavity, the third stage nematode molts (sheds its skin) to the fourth stage. As it does so, it releases the pellet of bacteria into the body fluid. The bacteria multiply rapidly and the nematode feeds on the bacteria and almost certainly engulfs the body fluid also. The nematode then develops to the adult stage. Males and females mate and the females lay eggs. The eggs hatch and the juveniles continue development through the adult stage. Again, mating takes place and the females lay eggs. These egg hatch and the juveniles develop to the third stage. These third-stage juveniles collapse the anterior portion of the intestine around a pellet of living bacteria and leave the cadaver in search of a new host insect. The length of life cycle is somewhat temperature-related, but takes place in about 4-10 days.

Since males and females are necessary for reproduction, both male and female juveniles must enter an insect for reproduction to occur, but a single nematode can cause death of the insect because the bacteria it releases causes septicemia. Before the work of Burman (Nematologica 28(1):62-70 1982), it was thought that the bacteria alone caused death of the insect, but it appears that the nematode may also play a role.

Although *S. scapterisci* is useful for the control of any pest insect species in the Order Orthoptera, the present invention is predicated on the discovery that *S. scapterisci* is particularly host-specific to mole crickets (i.e., Scapteriscus spp.), specifically *S. acletus*, *S. vicinus*, *S. abbreviatus* (imported mole crickets), *Neocurtilla hexadactyla* (native mole cricket) and to the house cricket, *Acheta domestica*, as an insect parasite and is particularly insecticidally specific to mole crickets and house crickets as opposed to other insects not in the Order Orthoptera.

Unexpectedly, *S. scapterisci* is relatively non-parasitic and non-insecticidal to most other insects, e.g., granulate cut worm, *Agriotis subterranea*, wax moth larvae, *Galleria melonella*, honeybees, *Apis mellifera*, etc. . . .

*S. scapterisci* nematodes collected in Uruguay were inoculated into mole crickets which were hand-carried to Florida. In Florida, populations of the nematode were increased in the mole crickets, *Scapteriscus vicinus* and *S. acletus*, and later in the house cricket, *Acheta domestica*. The population selected originally killed only 38% of the mole crickets; however, by serial passage through mole crickets, the kill rate was increased to 100%. These nematodes, or their progeny, were used for all studies.

Nematodes used for morphological studies were obtained as described below. Mole crickets were infected with the third-stage (infective stage) juvenile of *S. scapterisci*. After the mole crickets died, first generation adults were collected in 2-3 days, second generation adults in 5-7 days, and third-stage juveniles in 7-15 days. The nematodes were killed in warm water (40° C.), and mounted in water on glass slides with coverglass supports. In addition, many live nematodes or nematodes killed and stained with acid fuchsin were observed to confirm the presence and/or nature of some anatomic structure.

Nematodes prepared for scanning electron microscopy (SEM), were placed live in lactophenol at 43° C. for 30 minutes, transferred to a desiccator for two days, removed, rinsed with water, and then prepared by the method of Stone and Green, 1971 (Stone, A. R. and C. D. Green, 1971, A simple method of preparing nematodes for scanning electron microscopy, Nematologica 17:490-491). Specimens were examined in a Hitachi S450 SEM.

To prepare spicules and gubernacula for SEM, male nematodes of the first generation were placed in a petri dish containing water, killed by low heat and stored at room temperature. After 2-3 days when the bodies had softened due to decay, they were transferred to clean water, and, with two small needles, the rear portion of each nematode was torn open, the spicules and gubernaculum dissected out and washed free of debris by sloshing them about in water. Then the spicules and gubernaculum were picked up with a needle and placed on a previously-prepared SEM stub close to a hair used as a marker.

Cross hybridization studies were conducted using two different techniques. In one technique, a drop of blood (hemolymph) from a mole cricket was placed in a 35×10 mm sterile petri dish, and one third-stage juvenile of *S. scapterisci* and one of *S. carpocapsae* strain Breton added. The dish was placed in a plastic bag containing a paper towel saturated with water. The plastic bag was closed, tied and stored in the dark. The treatment was replicated 25 times.

In the second technique, two drops of blood were prepared as above, and 10 third-stage juveniles of *S. scapterisci* were placed in one drop and 10 third-stage juveniles of *S. carpocapsae* strain Breton were placed in the other drop. Then they were handled as above. The treatment was replicated 10 times for each nematode. The nematodes were observed daily and when the sexes could be distinguished, but before they became adults, all males in the dishes of *S. scapterisci* were removed and placed in a separate drop of blood. Similarly, the males of *S. carpocapsae* strain Breton were removed and placed in a separate drop of blood. Then the males of *S. scapterisci* were transferred to the drop of blood containing females of *S. carpocapsae* strain Breton, and males of *S. carpocapsae* strain Breton were transferred, to the drop of blood containing females of *S. scapterisci*. The nematodes were observed frequently to see if they mated and produced offspring. Nematodes of each species were retained in drops of blood in two dishes as controls.

Four species of insects in the Order of Lepidoptera, the fall army worm (*Spodoptera frugiperda*), the velvet bean caterpillar (*Anticarsia goemmatalis*, the granulate cut worm (*Feltia subterrania*), and the greater wax-moth larva (*Galleria mellonella* were used to compare the rate of kill by *S. scapterisci* to that of some other species and strains of Steinernema.

Two pieces of Whatman No. 2 filter paper were placed in a $100 \times 15$ mm petri, dish and 8,000 third-stage juvenile nematodes in 2 ml water, and 10 insects were added. Controls were prepared similarly but without nematodes. Treatments were replicated 4 times. After 2 days the number of dead insects was determined.

Measurements for first and second generation female are presented in Table 1, those for first and second generation males in Table 2 and those for third-stage juveniles in Table 3:

Holotype (male, first generation) Total length = 1554 $\mu$m; greatest width = 131 $\mu$m; length of stoma = 3.9 $\mu$m; width of stoma = 6 $\mu$m; head to excretory pore = 77 $\mu$m; head to nerve ring = 130 $\mu$m; head to end of esophagus = 189 $\mu$m; testes from reflection to terminus = 416 $\mu$m; body width at anus = 37.5 $\mu$m; tail length = 28 $\mu$m; spicule length = 89 $\mu$m; spicule width = 13.5 $\mu$m; gubernaculum length = 65 $\mu$m; gubernaculum width = 7.8 $\mu$m; mucron length = 4.5 $\mu$m.

Allotype (female, first generation) Total length = 4875 $\mu$m; greatest width = 200 $\mu$m; length of stoma = 7.8 $\mu$m; width of stoma = 11 $\mu$m; head to excretory pore = 78 $\mu$m; head to nerve ring = 181 $\mu$m; head to end of esophagus = 265 $\mu$m; body width at anus = 73 $\mu$m; V = 50%.

Description: Females, first generation: Body cuticle smooth, lateral fields and phasmids not observed. Head rounded, continuous with body, and bearing both labial and cephalic papillae. Lips six., united at base, each terminating in a labial papilla. The six labial papillae not evenly distributed when viewed en face. While, the 2 subventral and 2 subdorsal papillae are located as expected, the 2 lateral papillae are located ventrolaterally making the ventral an lateral papillae closer together than are the lateral and dorsal papillae. Apex of each papilla usually covered with a thin layer of whitish (electron lucent) material. Four cephalic papillae present, but not always distinct. Amphids not observed. Stoma very shallow, circular anteriorly, then becomes subtriangular.

Cheilorhabdions prominent, unusually thickened, appearing as a circular or hexagonal ring en face. Prorhabdions, just posterior to cheilorhabdions, also quite distinct. Posterior to prorhabdions, no other sclerotized structures observed. Esophagus typical of the Steinernematide, i.e., muscular throughout with a procorpus, slightly swollen, nonvalvate metacorpus, isthmus, and basal bulb with a small, but quite visible, valve. Nerve ring located in isthmus region of esophagus. Esophagointestinal valve long and prominent. Excretory pore located anteriorly to mid-metacorpus. Excretory duct unusually prominent forming a small loop midway between excretory pore and base of esophagus, then turning to right side of esophagus, or sometimes extending to anterior part of intestine then returning on ventral side of intestine at its junction with the esophagus; here appears an elliptically-shaped structure seemingly with a hole at the center. A uninucleate gland is located posteriorly to this structure but a junction of the excretory duct with the gland has not been observed. This elliptically-shaped, structure has been seen in almost every first generation female and is visible even with a dissecting microscope. Gonads didelphic, opposed; ovaries reflexed. Vulva appears as a transverse slit with a prominent double-flapped epiptygma. Vagina sclerotized, its length about ⅓ body width at vulva, and leading to paired uteri. Body width anterior to vulva always greater than that posterior to vulva. Tail somewhat variable in shape, but usually has a post-anal swelling ventrally and a mucron at its terminus; length of tail less than width of body at anus. Pigmy form of first generation females referred to for other species by Bovien (Bovien, P, 1937. Some types of association between nematodes and insects. Videnskabelige Meddelelser Fra Dansk Naturhistorisk Forening 101:1–114) not observed.

Female, second generation: Second generation female similar morphologically to that of first generation with the following exceptions: about one-half as long and two-thirds as wide, valve in basal bulb of esophagus more prominent, elliptically-shaped structure less prominent, tail, which tapers to a point bearing a mucron, longer than body width at anus.

Male, first generation: First generation male much smaller than first generation female, but anatomically the two are similar anteriorly. Body usually plump, nerve ring located in isthmus region of esophagus but exact position variable. Excretory duct not forming elliptically-shaped structure present in females. Posterior part of body curved ventrally. Body assumes a spiral shape when killed by minimal heat. Gonad one, testis reflexed. Spicules dark brown in color, paired, uniformly curved with head large and somewhat angular. Angle formed by shaft and blade of spicules averages 110 degrees (range 100–120). Shaft of spicules long when compared to those of other species of the genus, and appears to be encased in a sheath; blade tapers smoothly to end with posterior portion thinner than that for other species of Steinernema. In cross section, blade of spicule contains two lumina, but only one aperture was seen on ventral side close to tip. Aperture smaller than that in spicule of other species in the genus. Each spicule has two internal ribs with variable termination point proximally. Ribs appear to be strengthening structures of upper and lower walls between the two lumina of the blade. Gubernaculum boat-shaped, with anterior part thin, long and ventrally-curved and posterior end bifurcate. Compared to *S. carpocapsae* strain Breton, the anterior part of the gubernaculum of *S. scapterisci* is much longer. Spicules glide along gubernaculum in two grooves separated by a ridge. Cloaca on a raised area bearing an anterior flap, seen easily when the spicules are projected or retracted. Ten pairs and one single genital papillae observed with pairs 1 and 6 difficult to see. The single papilla is located ventrally and between pairs 4 and 5; pairs 1-9 are located ventrolaterally and pair 10 subdorsally. Tail bears a mucron, posterior region always curved ventrally.

Male, second generation: Second generation male similar morphologically to that of the first generation except that it is about two-thirds as long and one-half as wide and the spicules have an elongate head.

Juveniles, third stage: Measurements are given in Table 3. The third stage juvenile is the infective stage, and when newly formed, it is always enclosed in the cuticle of the second-stage juvenile as a sheath. However, the sheath is lost rather easily, even in storage, and thus may not always be present. Body thin., lip region not offset, oral aperture not observed. Esophagus degenerate and thus not seen clearly, but its basal bulb is elongate and has a valve. Lateral field with 6 incisures. Tail tapers, gradually dorsally but abruptly ventrally.

Type designations: Holotype (male of the first generation), slide number T-432t, USDA Nematode Collection, Beltsville, Md. Paratypes are distributed as follows: 10 males and 10 females of the first generation and several third-stage juveniles in lactophenol in a vial, vial number T-318p USDA Nematode Collection, Beltsville, Md.; 1 male and 1 female and 11 third-stage juveniles, slide numbers UCNC No. 2406 and UCNC No. 2407, respectively, California Collection of Nematodes, University of California, Davis, Calif.; 1 male and 1 female, and 10 third-stage juveniles, slide numbers T 99 N89-694, and T 100 N89-694 Florida Collection of Nematodes, Florida Department of Agriculture and Consumer Services, Gainesville, Fla. The nematode population is being maintained at the Nematology Lab, Entomology and Nematology Department, University of Fla., Gainesville, Fla.

In cross hybridization experiments, males and females never mated and thus no offspring were produced. In the controls, males and females mated and offspring were present after 10 days.

Except for *S. scapterisci*, all species of Steinernema tested, including all strains of *S. carpocapsae*, killed from 20- 100% of the test insects; *S. scapterisci* killed no more than 10% (Table 4). The difference in the percentage of wax moth larvae killed by other Steinernema spp. and *S. scapterisci* is significant since the wax moth larva can be used as a test insect to differentiate between *S. scapterisci* and all other species and strains of Steinernema known currently.

Preliminary work with isoelectric focusing electrophoresis showed that the protein patterns of *S. scapterisci* were different from those of Mexican and Breton strains of *S. carpocapsae*.

*Steinernema scapterisci* n. sp. can be distinguished from other species of Steinernema as follows: *S. glaseri* by the presence of a mucron on the tail of the male of *S. scapterisci*, and by the shorter third-stage infective juvenile of *S. scapterisci* (517-609 μm) compared to that of *S. glaseri* (860-1500 μm); from, *S. bibionis* and *S. intermedia* by the shorter third-stage juvenile (700-1000 μm for *S. bibionis* and 608-800 μm for *S. intermedia*); from *S. carpocapsae* by the ratio of head to excretory pore divided by tail length, this ratio is 0.73 (0.60-0.80) in *S. scapterisci* compared to 0.60 (0.54-0.66) in *S. carpocapsae* (Poinar, G.O., Jr., 1986, Recognition of Neoaplectana species (Steinernematidae: Rhabditida). Proc. Helminthol. Soc. Wash. 53:121-129); and by the shape of the tail of the third-stage juvenile; when relaxed, the tail of *S. scapterisci* usually curves ventrally forming an angle about 110 degrees with the body. The ratio of head to excretory pore/head to end of esophagus is 0.31 compared to 0.65 in *S. glaseri*, 0.45 in *S. bibionis*, 0.51 in *S. intermedia*, 0.26 in *S. carpocapsae*.

*S. scaptersci* n. sp. also can be separated from all other species by the following characters: The first generation female has large cheilorhabdions (about 4.8 μm thick by 5.8 μm long in lateral view of normal-sized females), an elliptically-shaped structure in the excretory canal, and a prominent double-flapped epitygma. Males of both generations have brown spicules which are pointed and taper smoothly to the end; distal end of the blade is narrow; shaft long and bearing a sheath; gubernaculum with long and upward-bent anterior part.

*S. scapterisci* n. sp. cannot be cultured on wax moth larvae (*Galleria mellonella*), but sometimes a few wax moth larvae will be killed by the nematode. When this occurs, the bodies of the wax moth larvae turn black while those killed by other species of Steinernema turn whitish or yellowish but never black. Other species of Steinernema develop very well in wax moth larvae. Finally, this nematode can be distinguished from other species by bioassay on 3 insects: fall army worm, velvet bean caterpillar, and wax moth larvae. In two days, other species of Steinernema will kill 100% of the test insects, but *S. scapterisci* will kill no more than about 10% thereof (Table 4).

TABLE 1

Measurements (in um) of first and second generation females of *Steinernema scapterisci* n. sp (n = 10)

| Character | First generation | | Second Generation | |
|---|---|---|---|---|
| | Mean (SD) | Range | Mean (SD) | Range |
| Body length | 4162 (540) | 3531-5156 | 2209 (223) | 1841-253 |
| Greatest width | 179 (13) | 159-203 | 123 (14) | 94-141 |
| Stoma length | 7.5 (1) | 6-9 | 6.7 (1.4) | 5-9 |
| Stoma width | 10 (3) | 9-12 | 8.9 (0.9) | 8-11 |
| EP | 89 (5) | 78-94 | 78 (6.8) | 66-88 |
| NR | 174 (13) | 153-194 | 169 (12) | 147-184 |
| ES | 242 (17) | 219-269 | 241 (15) | 222-266 |
| Tail length | 46 (8) | 34-59 | 58 (4) | 48-64 |
| Anal body width | 58 (9) | 41-72 | 47 (2.8) | 43-52 |
| Percentage vulva | 53 (2) | 50-54 | 52 (2) | 52-60 |
| EP:ES | 0.37 (0.03) | 0.32-0.41 | 0.32 (0.3) | 0.28-0.3 |

EP = Distance from anterior end to excretory pore
NR = Distance from anterior end to nerve ring
ER = Distance from anterior end to end of esophagus

TABLE 2

Measurements (in um) of first and second generation
females of *Steinernema scapterisci* n. sp. (n = 10)

| Character | First generation Mean (SD) | First generation Range | Second generation Mean (SD) | Second generation Range |
|---|---|---|---|---|
| Body length | 1728 (358) | 1319–2271 | 1147 (95) | 1031–1342 |
| Greatest width | 156 (49) | 97–231 | 73 (8) | 62–84 |
| Stoma length | 4.4 (1) | 3–5 | 4.3 (1) | 5–8 |
| Stoma width | 6.1 (1) | 5–8 | 6.0 (1.2) | 5–8 |
| EP | 71 (11) | 63–98 | 68 (7) | 50–75 |
| NR | 136 (11) | 120–152 | 121 (10) | 103–131 |
| ES | 187 (21) | 164–216 | 168 (13) | 138–181 |
| Testis flexure | 374 (52) | 306–447 | 205 (19) | 176–234 |
| Anal body width | 33 (5) | 31–45 | 33 (4) | 28–41 |
| Tail length | 25 (3) | 21–30 | 25 (3) | 22–30 |
| Spicule length | 83 (5) | 72–92 | 78 (3) | 75–83 |
| Spicule width | 13 (4) | 13–14 | 12 (1) | 11–14 |
| Gubernac. length | 65 (5) | 59–75 | 54 (3) | 47–59 |
| Gubernac. width | 8 (0.5) | 8–9 | 6 (0.7) | 5–8 |
| EP:ES | 0.36 (0.02) | 0.32–0.39 | 0.40 (0.06) | 0.29–0.52 |
| Mucron length | 4.3 (0.6) | 3.1–4.7 | 3.9 (0.6) | 3.1–4.6 |

EP = Distance from anterior end to excretory pore
NR = Distance from anterior end to nerve ring
ER = Distance from anterior end to end of esophagus

TABLE 3

Measurements (in um) of the third-stage juvenile
*Steinernema scapterisci* n. sp. (n = 20)

| Character | Mean | SD | Range |
|---|---|---|---|
| Body length | 572 | 27 | 517–609 |
| Greatest width | 24 | 4 | 18–30 |
| EP | 39 | 4 | 36–48 |
| NR | 97 | 1.1 | 83–106 |
| ES | 127 | 6 | 113–134 |
| Tail length | 54 | 3 | 48–60 |
| EP:ES | 0.31 | 0.03 | 0.27–0.40 |
| EP:Tail length | 0.73 | 0.06 | 0.60–0.80 |

EP = Distance from anterior end to excretory pore
NR = Distance from anterior end to nerve ring
ES = Distance from anterior end to end of esophagus

TABLE 4

Percentage of four species of lepidopterous
insects killed within 47 hours by Steinernema spp.

| Nematode | FAW | VBC | GCW | WML |
|---|---|---|---|---|
| *S. glaseri* | 100 | 90 | 50 | 100 |
| *S. bibionis* | 100 | 90 | 55 | 100 |
| *S. carpocapsae* | | | | |
| Breton | 100 | 100 | — | 100 |
| Italian | 100 | 100 | — | 100 |
| Mexican | 100 | 100 | 80 | 100 |
| Agriotos | 100 | 100 | 20 | 100 |
| All | 100 | 100 | — | 100 |
| *S. scapterisci* | 8 | 3 | 10 | 9 |
| Control | 0 | 0 | 0 | 0 |

+ Average of four trials
FAW = fall army worm; VCB = velvet bean caterpillar; GCW = granulate cut worm; WML = wax moth larvae.

EXAMPLE 1

*Steinernema scapterisci* was tested against potential host insects, except for honeybees, as follows: The test host insects were placed in petri dishes containing two filter papers. Then 8,000 to 12,000 infective third-stage juveniles of *S. scapterisci* in a water suspension were placed by pipette onto the filter papers. Lids were placed on the petri dishes and the dishes maintained in the dark at room temperature. A minimum of 30 insects were used per test. The specimens were observed each 24 hours to determine the number living and dead. Experiments were terminated after 48 to 72 hours. The numbers of dead insects were converted to percentages killed using Abbott's formula which is:

$$\frac{(X - Y)}{X} \times 100 = \% \text{ kill}$$

where
X = % living of untreated control insects;
Y = % living of nematode-treated insects.

Honeybee experiments were conducted in 5 cages for the treated and 5 cages for the controls with 20 honeybees in each cage. The experiment was repeated once. Five thousand nematodes were placed on water-saturated cotton contained in a petri dish. This served as the only source of water for the honeybees. Exposure to the nematodes occurred each time they visited the water source. The experiment was checked each 24 hours for living and dead honeybees and terminated after 72 hours. Abbott's formula was used to express percentage kill.

The results are set forth in Table 5.

TABLE 5

Insects killed by *S. scapterisci*

| Host | % Kill |
|---|---|
| Mole crickets (*Scapteriscus* spp.) | >90 |
| Field crickets (*Gryllus rubens*) | 14 |
| Honeybees (*Apis mellifera*) | 11 |
| Granulate cut worms (*Agriotis subterranea*) | 10 |
| Wax moth larvae (*Galleria melonella*) | 4 |

The above data show that *S. scapterisci* has a high degree of specificity to mole crickets. The data are significant, also, in that only 4% of wax moth larvae were killed, whereas wax moth larvae are used as hosts to produce all other strains of the nematode in vivo.

EXAMPLE 2

Field Tests of *S. scapterisci*

Field releases of the nematode were made in 1985 in two 7×7 meter (=49 square meters) plots to determine if the nematode could survive in the Florida environment and to obtain some information on rate of kill of mole crickets. The nematodes were applied by two different methods at a rate of 200,000 infective third-stage juveniles per square meter. One method was to mix the nematodes in water and apply them from sprinkling cans onto the plots. The other method was to bury per square meter four dead mole crickets which had been infected with the nematode in the laboratory. (We obtained about 50,000 infective stage juvenile nematodes from each infected mole cricket). The initial kill rates in these plots averaged about 30% of those mole crickets caught in pitfall traps placed in the center of each plot. The kill rates dropped off to about 10% of those mole crickets trapped over the next year. Thus, the nematode survives both summers and winters in Florida, but the plots were too small to avoid reinfestation by mole crickets from outside the plots.

Water or other aqueous media and infected, dead mole crickets have been used as means for distributing the nematodes. There is no reason that other carriers which do not cause the nematodes to die from desiccation would not be suitable. An attractant for mole crickets (e.g., COAX®, sucrose, maltose, malt extract or molasses) may be included in the composition.

An alternative method is to trap mole crickets, infect them with the nematode, and then release them before they become too sick to be active, so that they will distribute the nematode outward from the release site and also in the soil where mole crickets bury. Another method to use during the flight season of the mole crickets is to infest a small plot of ground (5×5 meters, for example) with large numbers of nematodes, perhaps 400,000 or more per square meter, place an electronic caller (a device which mimics the song of mole crickets to which they are attracted) in the center of the area and let the mole crickets become infected when they land in the infested area. When the electronic caller is turned off, the infected mole crickets will fly from the site and thus disperse the nematode when they die. Other mole crickets will, in turn, become infected from those sites and increase the dispersion area of the nematode when those mole crickets die.

Generally, amounts of composition (nematodes plus carrier) are applied so as to provide from about 100,000 to about 200,000 nematodes per square meter of leaf or soil.

A further embodiment of the invention comprises the use of a strain of *S. scapterisci* having an enhanced insecticidal activity. The new strains are developed by passage of a first infective third-stage of the nematode through the targeted insect, i.e., by infecting a targeted species of insect with infective third-stage juveniles of the nematode. Some of those nematodes successfully penetrate into the hemocoel and reproduce limitedly inside the body. Some of their offspring also reproduce in the same insect cadaver and a few of their progeny exit the cadaver as infective third-stage juveniles. These juveniles may optimally be inoculated into e.g., house crickets (*Acheta domestica*) to increase their numbers. The third-stage juveniles that emerge from house cricket cadavers are exposed to other targeted species of insects. A greater number penetrate into the body and reproduce the second time resulting in a greater number of third-stage juveniles exiting from the targeted species cadavers. If numbers are still low, however, these can be inoculated into house crickets to increase their numbers.

It is preferred to conduct a serial passage of the nematodes through the targeted insect, i.e., repeating at least once the steps of (1) infecting insects of the targeted species with nematodes, and (2) collecting infective third-stage juveniles which emerge from insects killed by the repeated infection, wherein the repeated infection is effected with the infective third-stage juveniles produced previously; the infective third-stage juveniles produced by the repeated infection having a greater degree of insecticidal activity than those produced previously.

The steps of infection and collection of infective third-stage juveniles are effected until a maximum degree of insecticidal activity in the collected third-stage juveniles is achieved.

The host species of insect utilized to increase the numbers of infective third-stage juveniles may comprise any insect life stage that is a suitable host of the nematode. Such third-stage juvenile nematodes also may be increased in vitro by using a suitable culture medium for the bacterium on which they feed. Such a medium is disclosed in U.S. Pat. No. 4,178,366, the disclosure of which is incorporated herein by reference. Another good medium can be made from vegetable or animal oil, hog or beef liver and water applied to an inert carrier, e.g., cellulose sponge. One such formulation is 50 grams of macerated liver, 2 milliliters of cooking oil and 250 ml of water mixed and absorbed into 20 grams of sponge.

EXAMPLE 3

The original strain of *S. scapterisci* collected from the field killed 38% of the mole cricket species, *Scapteriscus acletus*, into which they were inoculated. The infective third-stage juveniles which emerged from the dead mole crickets were inoculated into other mole crickets, both *S. acletus* and *S. vicinus*. Progeny from these nematodes have been used in all other tests.

EXAMPLE 4

Experiments were conducted in 3- or 5-gallon size buckets of soil to compare different methods of adding infective stage *S. scapterisci* to the soil and the period of time over which kill of mole crickets would occur without adding more nematodes. The Uruguayan strain of nematode was used.

Treatments were: 1 infected mole cricket, 2 infected mole crickets, 12,000 nematodes sprayed on the soil surface and untreated control. It was calculated that about 50,000 nematodes would emerge from each mole cricket carcass but would not move far from the carcass. The spray application was equivalent to 180,000 nematodes per square meter.

Ten mole crickets (uninfected) were released into each bucket. Ten days later the number of dead and living mole crickets was determined and the percentage kill calculated based on Abbott's formula. Again, 10 uninfected mole crickets were released in the buckets and the process repeated for a total of four releases.

The results are set forth in Table 6.

TABLE 6

| Inoculum | Release | | | |
|---|---|---|---|---|
| | 1 | 2 | 3 | 4 |
| | Adjusted % kill of *Scapteriscus vicinus* | | | |
| 1 infected mole cricket | 29 | 43 | 18 | 10 |
| 2 infected mole crickets | 38 | 47 | 12 | 12 |
| 12,000 nematodes | 34 | 70 | 27 | 9 |
| | Adjusted % kill of *Scapteriscus acletus* | | | |
| 1 infected mole cricket | 12 | 26 | 12 | 17 |
| 2 infected mole crickets | 3 | 22 | 4 | 0 |

TABLE 6-continued

| Inoculum | Release | | | |
|---|---|---|---|---|
| | 1 | 2 | 3 | 4 |
| 12,000 nematodes | 19 | 48 | 12 | 0 |

The methods, composition, and products of the present invention are highly advantageous in that the nematodes employed, unlike those currently in use, do reproduce in the target insect species and, hence, recycle in nature to continue controlling the insect over long periods of time.

In plot tests (50 sq. m.) conducted over a span of years, the population of, for example, mole crickets have declined about 95% after a single application of the nematodes and have remained at that level for four years after application. Moreover, in these tests, the nematode has been recovered some ten miles from the nearest release site.

We claim:

1. A method of biologically controlling pest mole crickets of the Order Orthoptera comprising contacting so as to infect said insects with an insecticidal amount of infective third stage of *Steinernema scapterisci* nematodes having ATCC no. 75197.

2. The method of claim 1 wherein said infective third stage of *Steinernema scapterisci* nematodes is produced by passage of a first infective third stage of said nematodes through said insects to produce a second infective third stage of said nematodes having a greater degree of insecticidal activity than said first infective third stage.

3. The method of claim 2 wherein said first infective third stage of said nematodes is serially passaged through said insects to produce said infective third stage having a greater degree of insecticidal activity than said first infective third stage.

* * * * *